(12) United States Patent
Andersen et al.

(10) Patent No.: US 7,541,019 B2
(45) Date of Patent: Jun. 2, 2009

(54) PROCESS FOR THE PRODUCTION OF DTPA-BIS ANHYDRIDE

(75) Inventors: Eli Ryssdal Andersen, Spangereid (NO); Lars Terje Holmaas, Spangereid (NO); Vidar Olaisen, Spangereid (NO)

(73) Assignee: GE Healthcare AS, Oslo (NO)

( * ) Notice: Subject to any disclaimer, the term of this patent is extended or adjusted under 35 U.S.C. 154(b) by 0 days.

(21) Appl. No.: 10/582,698

(22) PCT Filed: Dec. 16, 2004

(86) PCT No.: PCT/NO2004/000389

§ 371 (c)(1),
(2), (4) Date: Jun. 13, 2006

(87) PCT Pub. No.: WO2005/058846

PCT Pub. Date: Jun. 30, 2005

(65) Prior Publication Data

US 2007/0117977 A1 May 24, 2007

(30) Foreign Application Priority Data

Dec. 19, 2003 (NO) .................................. 20035745

(51) Int. Cl.
*A61K 51/00* (2006.01)
*A61M 36/14* (2006.01)
(52) U.S. Cl. ..................................................... 424/1.65
(58) Field of Classification Search ................. 424/1.65
See application file for complete search history.

(56) References Cited

U.S. PATENT DOCUMENTS 3,660,388 A * 5/1972 Riehen ........................ 544/86
4,698,263 A * 10/1987 Wagner et al. ........... 428/402.2
4,707,453 A 11/1987 Wagner et al.
4,822,594 A * 4/1989 Gibby ........................ 424/9.35
5,508,388 A * 4/1996 deLearie et al. ............... 534/16

FOREIGN PATENT DOCUMENTS

CS 272584 B1 * 11/1991
EP 0183760 6/1986

OTHER PUBLICATIONS

Miyamoto, M. et al., "Design and Preparation of Gadolinium-Reservoir Microcapsules for Neutron-Capture Therapy by Meanse of the Wurster Process" Chemical and Pharmaceutical Bulletin, Phar. Society of Japan, Tokyo, JP, vol. 45, No. 12 Dec. 1997, pp. 2043-2050.
Eckelman, W.C., et al., "New Compounds: Fatty Acid and Long Chain Hydrocarbon Derivatives Containing a Strong Chelating Agent" Journal of Pharmaceutical Sciences, American Pharmaceutical Assoc. Wash. US, vol. 64, No. 4 Apr. 1975, pp. 704-706.
PCT/NO2004/000389 Int'l Search report/written opinion dated May 2005.

* cited by examiner

*Primary Examiner*—Michael G Hartley
*Assistant Examiner*—Melissa Perreira
(74) *Attorney, Agent, or Firm*—Craig Bohlken

(57) ABSTRACT

Process for the production of DTPA-bis(anhydride) by reacting DTPA with acetic anhydride in pyridine under elevated temperature wherein the molar amount of pyridine is equal to or less than 6 times the molar amount of DTPA.

16 Claims, No Drawings

PROCESS FOR THE PRODUCTION OF DTPA-BIS ANHYDRIDE

This application is a filing under 35 U.S.C. 371 of international application number PCT/NO2004/000389, filed Dec. 16, 2004, which claims priority to application number 20035745 filed Dec. 19, 2003, in Norway the entire disclosure of which is hereby incorporated by reference.

The present invention provides an improved process for the production of Diethylenetriaminepentaacetic acid-bis(anhydride) (DTPA-bis(anhydride)). DTPA-bis(anhydride) is an important intermediate used in the production of drug substances e.g. for therapy and diagnosis. One such class of commercial products are chelants (chelating agents). Chelants such as DTPA-bis-metylamide and DTPA-bis(2-metoxyethylamide) are useful as sequestering agents e.g. for metal detoxification of living humans and animals and non-living matter and as additives to a vide variety of products. Chelants are also well known as intermediates for the production of metal chelates. Chelates of paramagnetic metals such as gadolinium find their use as contrast agents for Magnetic Resonance Imaging (MRI). Examples of commercial products useful as contrast agents for MRI are Omniscan™ of Amersham Health AS and Optimark™ of Mallinckrodt, Inc.

Processes for the for the production of DTPA-bis(anhydride) are well known in the state of art.

U.S. Pat. No. 3,660,388 teaches a process for the production of bis-dioxo-morpholine derivatives. These derivatives correspond to bis-anhydrides of alkylene amine carboxylic acids such as the bis-anhydrides of EDTA and DTPA. Specifically example 9 of this patent teaches the-production of N,N-bis(β-[2,6-dioxo-morpholinyl(4)]-ethyl)-N-carboxymethylamine, hereinafter denoted DTPA-bis(anhydride) from DTPA, acetic acid anhydride and pyridine. The reactants are stirred for 48 hours at 60° C. or for 5 minutes at 125° C. The amount of pyridine is about 6.5 moles per mole DTPA.

U.S. Pat. No. 4,822,594 teaches in Example 1 the preparation of DTPA bis(anhydride) where DTPA is mixed with anhydrous pyridine and acetic anhydride is added. The reaction runs for 20 hours at 65° C. The amount of pyridine is about 6.2 moles per mole DTPA.

U.S. Pat. No. 4,698,263, in col. 12 lines 1 to 7, and U.S. Pat. No. 4,707,453, in col. 11 lines 40 to 46, both describe the same preparation of DTPA -bis(anhydride) from DTPA, acetic acid anhydride and pyridine. The reaction is run for 18 hours at reflux temperature under a $N_2$ atmosphere. The amount of pyridine is about 7.5 moles per mole DTPA.

EP 0183760 B1 teaches in Example 1, i), (a) the formation of DTPA -bis(anhydride) from DTPA, acetic acid anhydride and pyridine. The reaction is run for 24 hours at 55° C. The amount of pyridine is about 6.3 moles per mole DTPA.

It is known from the state of art that pyridine is toxic and relatively expensive and that there is a desire to reduce the amount of pyridine to a minimum, see U.S. Pat. No. 5,508,388, col. 3, lines 23 to 27. It is likewise a desire to use a minimum number of reactants, hence the addition of acetonitrile as used in U.S. Pat. No. 5,508,388 is not desirable. Acetonitrile is poisonous and should be avoided whenever possible.

The object with this invention is hence to provide a process for the production of DTPA -bis(anhydride) which involves a minimum of reactants. In particular the use of toxic reactants should be avoided or reduced to a minimum. It is likewise a desire to reduce the use of costly reactants to a minimum. At the same time it is important to maintain a high yield, to keep the reaction time and temperature within controllable limits and to obtain a product that can be readily used in the next process step. The product should preferably be obtained without time-consuming purification or in a form that can be easily purified for sale or a state feasible for further processing.

It has surprisingly been found that DTPA-bis(anhydride) can be produced by reacting DTPA with acetic anhydride in pyridine under elevated temperature where the molar amount of pyridine is equal to or less than 6 times the molar amount of DTPA. Notably the use of acetonitrile is avoided and the amount of pyridine is reduced under the level known from the prior art when DTPA is reacted with acetic anhydride and pyridine alone.

The present invention is defined in the patent claims. Specific details in carrying out the invention are evident from the specific examples 1 to 3, 5 and 7 herein.

Production of chelants useful in industry and in particular as therapeutics and diagnostics are described in examples 4 and 6 herein. The chelants find use as sequestering agents e.g. for metal detoxification of living humans and animals and non-living matter and as additives to a vide variety of products.

The chelant DTPA-BMA of examples 4 and 6 when chelated with $Gd^{3+}$ is the active substance in the commercially available MR (Magnetic Resonance) contrast medium Omniscan™ of Amersham Health AS. The production of DTPA-BMA and Gd DTPA-BMA is further described in U.S. Pat. Nos. 4,859,451, 4,687,659 and 5,087,439 that are hereby incorporated by reference.

The chelant versetamide (DTPA-bis(2-metoxyethylamide)) when chelated with $Gd^{3+}$ is the active substance in the commercially available MR contrast medium Optimark™ of Mallinckrodt, Inc. The production of Gadoversetamide is described in U.S. Pat. No. 5,508,388.

U.S. Pat. No. 3,660,388 teaches that the bis(anhydrides) are also useful in the curing of epoxy groups containing organic compounds.

In its broadest aspect the invention thus relates to a process for the production of DTPA-bis(anhydride) by reaction of DTPA with acetic anhydride in pyridine under elevated temperature and where the amount of pyridine is reduced relative to the processes known from the state of art. The ratio of the molar amount of pyridine to the molar amount of DTPA shall be equal to or less than 6.

In a preferred aspect of the invention the ratio of molar amount of pyridine to the molar amount of DTPA is significantly less than 6, for example 5 or 4 or more specifically is equal to or less than 3. It is found that the reaction rate becomes only insignificantly lower at a rate of 3 compared with a rate of 8.1, and is well within the acceptable area for an industrial process. The content of un-reacted DTPA remains low.

In a further preferred aspect of the invention the ratio of molar amount of pyridine to the molar amount of DTPA is significantly less than 3, for example about 2 or more specifically is equal to or less than 1. Even at this low molar rate the reaction rate is acceptable as well as is the content of un-reacted DTPA. It is even possible to run the process at a ratio of 0.5, however at this ratio the reaction rate seems to be lower.

The molar amount of acetic anhydride could also be optimized relative to the molar amounts of pyridine and DTPA. The, stoechiometric amount is 2 moles acetic anhydride per mole DPTA, but it appears that-acetic anhydride should be added in excess, more than 7 times the molar amount of DTPA is feasible. More preferred is a molar amount of 7 to 5 times the molar amount of DTPA, and even more preferred an amount between 5 and 3 times the molar amount of DTPA.

The optimum amount seems to be about 3 moles acetic anhydride per mole DTPA, although an amount only slightly higher than the stoechiometric amount of 2 moles is workable.

A high molar excess of acetic anhydride relative to the pyridine and DTPA content seems to lead to a decrease in the reaction rate. Without being bound to theory, one can assume that this is due to a dilution effect for the pyridine and DTPA reagents. A dilution effect seems to be most pronounced at lower pyridine concentrations.

Hence, in a specifically preferred aspect a molar amount of acetic anhydride of about 3 times the molar amount of DTPA is used.

In a particularly preferred aspect of the invention the molar amount of acetic anhydride is about 3 times the molar amount of DTPA and the amount of pyridine is from 3 times to approximately 1 time the molar amount of DTPA.

The reaction temperature also has impact on the overall reaction rate in the production of DTPA-bis(anhydride) from DTPA. Conventionally this reaction is run at a temperature from 60° C. to 70° C. It has been found that when the process is run at 80° C., the reaction rate increases significantly without an increase in the impurity level. The impurity level is even decreased when the process is run at approximately 80° C.

In a further aspect of the invention the process for the production of a DTPA-bis(anhydride) is performed at a reaction temperature of above 65° C., more preferred above 70° C. and even more preferred at 80° C. or above. In a specifically preferred aspect the reaction temperature is approximately 80° C.

In a particularly preferred aspect of the invention the molar amount of acetic anhydride is about 3 times the molar amount of DTPA and the amount of pyridine is from 3 times to approximately 1 time the molar amount of DTPA when the process is run at a temperature of about 80° C.

The invention will now be illustrated further with reference to the following non-limiting examples.

The abbreviations have the following meaning:

NIR—Near Infra Red Spectroscopy
DTPA—Diethylenetriaminepentaacetic acid
BMA—Bismethylamine
MMA—Monomethylamine
h—Hour
L—litre
Wt %—weight percent All temperatures are in Celsius degrees (° C.)

EXAMPLE 1

Preraration of DTPA-bis(anhydride)

DTPA (100 g, 0.25 mole), acetic anhydride (various amounts), and pyridine (various amounts) were combined in a 1 L, 3-necked flat-bottomed reactor fitted with a thermometer, a mechanical stirrer, and reflux condenser cooled with cold water. The reactor was fitted with a water jacket, and the temperature in the jacket was controlled by a water bath. The mixture was heated with stirring to 70° C. Samples were taken from the reaction mixture at 0.5, 1, 2, 3, 4, and 5 h after the temperature had reached 70° C. All samples were filtered on a Büchner funnel, washed with acetonitrile and dried at vacuum. All samples and a sample of the end product were analysed by NIR with respect to DTPA content. After 10 h the reaction mixture was cooled to room temperature. The mixture was then filtered on a Büchner funnel and washed with approximately 70 ml acetonitrile. The product was collected and dried with vacuum at 50° C.

EXAMPLE 2

Effect of Pyridine and Acetic Anhydride Concentration

Experiments following the procedure of Example 1 were carried out to optimise the reaction with respect to the amount of pyridine and acetic anhydride on the reaction rate and DTPA content in the final product (Tables 1 and 2). We assumed a first order reaction when calculating the reaction rate.

Effect of Pyridine Concentration:

From the data of table 1 it will be seen that the reaction rate was decreasing with decreasing pyridine concentration. However, at a reaction time of 10 h the conversion was completed for pyridine concentration down to 1.0 mole/mole DTPA. For the experiment with the lowest pyridine concentration of 0.5 mole/mole DTPA the conversion was not completed after 10 h, and thus, the concentration of DTPA was significantly higher for this experiment. A further decrease of pyridine may be possible if the reaction time is prolonged and/or the temperature is raised.

TABLE 1

Reaction rate and purity for different pyridine concentration levels. Concentration of acetic anhydride was constant for all experiments (3.0 mole acetic anhydride/mole DTPA)

| Pyridine amount (mole/mole DTPA) | Reaction rate ($h^{-1}$) | DTPA content (wt %) |
|---|---|---|
| 8.1 | 1.3 | 0.85 |
| 3.0 | 0.91 | 0.82 |
| 1.0 | 0.63 | 0.71 |
| 0.5 | 0.39 | 2.24 |

Effect of Acetic Anhydride Concentration:

The effect of variations in the acetic anhydride concentration is Illustrated in Table 2. The optimised acetic anhydride concentration seems to be 3 moles/mole DTPA. The stoechiometric amount in the conversion of DTPA to DTPA-bis(anhydride) is 2 mole/mole DTPA, but it seems that acetic anhydride should be added in slight excess. However, a high excess of acetic anhydride leads to a decreased reaction rate, and thereby, higher concentration of the raw material in the product. This effect is probably because high concentration of acetic anhydride leads to a dilution effect for the reagents DTPA and pyridine. This dilution effect is observed also for higher pyridine concentrations, but it seems to be most pronounced for low pyridine concentrations.

TABLE 2

Reaction rate and purity for different acetic anhydride concentration levels. Concentration of pyridine was constant for all experiments (1.0 mole pyridine/mole DTPA)

| Acetic anhydride concentration (mole/mole DTPA) | Reaction rate ($h^{-1}$) | DTPA content (wt %) |
|---|---|---|
| 7.4 | 0.39 | 2.37 |
| 5.3 | 0.45 | 3.60 |
| 3.0 | 0.63 | 0.71 |
| 2.1 | 0.54 | 3.60 |

TABLE 3

Summary of the concentration of impurities in the product produced at a molar ratio of 1 mole DTPA to 1 and 10 mole pyridine and 3 moles acetic anhydride where the reaction is run according to Example 1. DTPA-MMA was measured by $^1$H NMR. Concentration of impurities for two pyridine concentration levels

| Molar ratio DTPA:Pyridine | DTPA (wt %) | DTPA-MMA (wt %) | Pyridine (ppm) |
|---|---|---|---|
| 1.0:10.0 | 1.03 | 4.4 | 0.12 |
| 1.0:1.0 | 0.71 | 2.0 | 0.0 |

EXAMPLE 3

Effect of Temperature

When the reaction of example 1 was run at 80° C. the reaction rate showed a significant increase. At 80° C. the reaction rate was 2.0 h$^{-1}$, whereas the rate was 0.63 h$^{-1}$ when the reaction was run at 70° C. The concentration of impurities was slightly lower for the reaction run at 80° C.

EXAMPLE 4

Synthesis of DTPA-BMA from DTPA-bis(anhydride)

Some of the batches of DTPA-bis(anhydride) were used to produce DTPA-BMA, which is the next step in the process for the production of Gadodiamid, the drug substance of Omniscan™. Table 4 presents the results for the quality parameters of DTPA-BMA from DTPA-bis(anhydride) produced at three different content levels of pyridine. Decreased pyridine content generally gave similar content of the impurities, and all these impurities were inside the specification for DTPA-BMA.

TABLE 4

| Concentration of raw material for the DPTA-bis(anhydride) formation (mole/mole DTPA) | | HPLC concentration (area %) | | |
|---|---|---|---|---|
| Pyridine | Acetic anhydride | DTPA | DTPA-MMA | DTPA-BMA |
| 10.0 | 3.7 | 0.1 | 1.05 | 98.8 |
| 3.0 | 3.0 | 0.1 | 0.6 | 99.3 |
| 1.0 | 3.0 | 0.1 | 0.4 | 99.3 |

EXAMPLE 5

Preparation of DTPA-bis(anhydride)

The experiments were run in a 5 L lab reactor, and the batch sizes were increased 10-26 fold compared to the previous experiments of Examples 1 to 3.

The experiments were run at 70° C. for 10 hours, and the acetic acid concentration was 3.5 mole/mole DTPA. The pyridine concentration varied from 1.0 to 10.0 mole/mole DTPA. The results from these experiments are shown in table 5.

TABLE 5

| Pyridine concentration (mole/mole DTPA) | Batch size DTPA (kg) | Concentration impurities | |
|---|---|---|---|
| | | DTPA (wt %) | DTPA mono(anhydride) (mole %) |
| 1.0 | 2.0-2.6 | 1.2 | 1.3 |
| 3.0 | 2.0 | 1.1 | — |
| 5.0 | 1.0-2.0 | 1.1 | 2.0 |
| 7.5 | 1.0 | 1.2 | 1.8 |
| 10 | 1.0 | 1.4 | — |

This experiment reveals that upscaling of the reaction volume provide DTPA-bis(anhydride) of good quality. The reduction of the pyridine content does not impact the purity of the product measured by its content of unreacted DTPA and DTPA mono(anhydride) formed.

EXAMPLE 6

Production of DTPA-BMA from DTPA-bis(anhydride)

DTPA bis(anhydride) produced according to example 5 was used to produce DTPA-BMA in ordinary lab scale (batch size: 100 g) and for the reason explained in Example 4. Decreased pyridine content generally gave similar content of the impurities as for a high content of pyridine, and all the impurities levels were inside the specification for DTPA-BMA.

Table 6 shows the results from these experiments.

TABLE 6

| Pyridine concentration for the DTPA bis(anhydride) formation (mole/mole DTPA) | Assay (wt %) | HPLC concentration (area %) | | |
|---|---|---|---|---|
| | | DTPA | DTPA-BMA | DTPA-MMA |
| 1.0 | 100.1 | 0.4 | 99.3 | 0.3 |
| 3.0 | 100.0 | 0.1 | 99.5 | 0.5 |
| 5.0 | 99.6 | 0.1 | 99.6 | 0.3 |
| 10 | 99.6 | 0.1 | 99.4 | 0.5 |

EXAMPLE 7

Full Scale Production of DTPA bis(anhydride) and DTPA-BMA with Reduced Pyridine Concentration in the Formation of DTPA bis(anhydride)

DTPA bis(anhydride) is traditionally produced using a pyridine concentration of 10 mole/mole DTPA. The batch size is about 800 kg DTPA. Several batches of this size were produced with a pyridine concentration of 5.0 mole/mole DTPA. The yield of DTPA bis(anhydride) increased by approximately 1.5%. The purity of DTPA-BMA produced from the DTPA bis(anhydride) obtained were inside normal variation limits.

What is claimed is:

1. A process for the production of DTPA-bis(anhydride) characterized in that DTPA is reacted with acetic anhydride in pyridine under elevated temperature and that the molar amount of pyridine is equal to or less than 4 times the molar amount of DTPA with the proviso that acetonitrile is not added to the reaction.

2. The process of claim 1 wherein the molar amount of pyridine is equal to or less than 3 times the molar amount of DTPA.

3. The process of claim 1 wherein the molar amount of pyridine is equal to or less than 1 time the molar amount of DTPA.

4. The process of claim 1 wherein the molar amount of pyridine is at least 0.5 times the molar amount of DTPA.

5. The process of claim 1 wherein the molar amount of pyridine is approximately the same as the molar amount of DTPA.

6. The process of claim 1 wherein the molar amount of acetic anhydride is in excess of the molar amount of DTPA.

7. The process of claim 6 wherein the molar amount of acetic anhydride is more than 7 times the molar amount of DTPA.

8. The process of claim 6 wherein the molar amount of acetic anhydride is more than 5 times the molar amount of DTPA.

9. The process of claim 6 wherein the molar amount of acetic anhydride is more than 3 times the molar amount of DTPA.

10. The process of claim 6 wherein the molar amount of acetic anhydride is more than 2 times the molar amount of DTPA.

11. The process of claim 6 wherein the molar amount of acetic anhydride is about 3 times the molar amount of DTPA.

12. The process of claim 1 wherein the molar amount of acetic anhydride is about 3 times the molar amount of DTPA and the amount of pyridine is approximately the same as the molar amount of DTPA.

13. The process of claim 1 wherein the reaction temperature is above 65° C.

14. The process of claim 1 wherein the reaction temperature is above 70° C.

15. The process of claim 1 wherein the reaction temperature is at 80° C. or above.

16. The process of claim 1 wherein the molar amount of acetic anhydride is about 3 times the molar amount of DTPA, the amount of pyridine is approximately the same as the molar amount of DTPA and wherein the reaction temperature is approximately 80° C.

* * * * *